(12) United States Patent
Ghosh et al.

(10) Patent No.: US 10,918,870 B2
(45) Date of Patent: Feb. 16, 2021

(54) ATRIAL LEAD PLACEMENT FOR TREATMENT OF ATRIAL DYSSYNCHRONY

(71) Applicant: Medtronic, Inc., Minneapolis, MN (US)

(72) Inventors: Subham Ghosh, Blaine, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 335 days.

(21) Appl. No.: 15/914,396

(22) Filed: Mar. 7, 2018

(65) Prior Publication Data
US 2019/0275339 A1 Sep. 12, 2019

(51) Int. Cl.
*A61N 1/37* (2006.01)
*A61N 1/39* (2006.01)
(Continued)

(52) U.S. Cl.
CPC .......... *A61N 1/3714* (2013.01); *A61B 5/4848* (2013.01); *A61N 1/0587* (2013.01); *A61N 1/3684* (2013.01); *A61N 1/37223* (2013.01); *A61N 1/39622* (2017.08); *A61B 5/0428* (2013.01); *A61B 5/0452* (2013.01);
(Continued)

(58) Field of Classification Search
CPC .............. A61N 1/3714; A61N 1/39622; A61N 1/0587; A61N 1/3684; A61N 1/37223; A61B 5/4848; A61B 5/04085; A61B 5/0428; A61B 5/0452; A61B 5/0456; A61B 5/6805; A61B 5/6831; A61B 5/746; A61B 5/7475
See application file for complete search history.

(56) References Cited

U.S. PATENT DOCUMENTS 4,233,987 A 11/1980 Feingold
4,402,323 A 9/1983 White
(Continued)

FOREIGN PATENT DOCUMENTS

CN 1043621 A 7/1990
CN 1253761 A 5/2000
(Continued)

OTHER PUBLICATIONS

PCT/US2019/021165) PCT Notification of Transmittal of the International Search Report and the Written Opinion of the International Searching Authority, dated Jul. 17, 2019, 13 pages.
(Continued)

*Primary Examiner* — Lindsey G Wehrheim
(74) *Attorney, Agent, or Firm* — Mueting Raasch Group

(57) ABSTRACT

A system and method of positioning an atrial pacing lead for delivery of a cardiac pacing therapy that includes sensing electrical activity of tissue of a patient from a plurality of external electrodes and determining a distribution of bi-atrial activation in response to the sensed electrical activity. A target site for delivering the atrial pacing therapy is adjusted based on a change in bi-atrial dyssynchrony that is determined in response to the determined distribution of bi-atrial activation, and placement of the atrial pacing lead for delivery of the atrial pacing therapy is determined in response to the adjusting.

24 Claims, 9 Drawing Sheets

(51) Int. Cl.

| | | |
|---|---|---|
| *A61N 1/372* | (2006.01) | |
| *A61N 1/05* | (2006.01) | |
| *A61N 1/368* | (2006.01) | |
| *A61B 5/00* | (2006.01) | |
| *A61B 5/0456* | (2006.01) | |
| *A61B 5/0408* | (2006.01) | |
| *A61B 5/0428* | (2006.01) | |
| *A61B 5/0452* | (2006.01) | |

(52) U.S. Cl.
CPC ......... *A61B 5/0456* (2013.01); *A61B 5/04085* (2013.01); *A61B 5/6805* (2013.01); *A61B 5/6831* (2013.01); *A61B 5/746* (2013.01); *A61B 5/7475* (2013.01)

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,937,897 B2 | 8/2005 | Min et al. |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,027,876 B2 | 4/2006 | Casavant et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |

(56) References Cited

U.S. PATENT DOCUMENTS

| | | |
|---|---|---|
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |

(56) References Cited

U.S. PATENT DOCUMENTS

| | | |
|---|---|---|
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1* | 2/2016 | Ghosh ............... A61B 5/04085 607/18 |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | 2012/067935 A1 | 5/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |
| WO | 2017178851 A3 | 10/2017 |

OTHER PUBLICATIONS

International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.

(56) References Cited

OTHER PUBLICATIONS

International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4): 376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9): 1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron CARELINK ENCORE® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010;121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.

(56) References Cited

OTHER PUBLICATIONS

Turner et al, "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

ATRIAL LEAD PLACEMENT FOR TREATMENT OF ATRIAL DYSSYNCHRONY

The disclosure herein relates to implantable medical systems and methods for use in the evaluation of atrial lead placement for delivery of atrial pacing therapy for treatment of atrial dyssynchrony.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

Patients with atrial dyssynchrony have wide P-waves and slower atrial conduction which may result in delayed atrial kick and lessened contribution of atrial kick to filling which can compromise ventricular function (heart failure). Atrial dyssynchrony may also be a cause for atrial arrhythmias and atrial fibrillation. Atrial pacing therapy like targeting Bachmann's bundle for synchronized atrial activation or other means of multi-site atrial stimulation may help restore atrial synchrony and lead to better outcomes in these patients including bettering heart failure symptoms and potentially reducing burden of atrial arrhythmias. Therefore, there is a growing interest in a method and apparatus for improving determination of a desired location or locations from which to delivery pacing therapy from within the atrium that results in overall improvement of bi-atrial synchrony.

SUMMARY

The exemplary systems, methods, and interfaces described herein may be configured to assist a user (e.g., a physician) in evaluating a patient and/or evaluating placement of a pacing lead for delivering a pacing therapy during and/or after implantation of cardiac therapy apparatus. In one or more embodiments, certain portions of the systems, methods, and interfaces may be described as being noninvasive. For example, in some embodiments, the systems, methods may use electrical measurements taken noninvasively using, e.g., a plurality of external electrodes attached to the skin of a patient about the patient's torso.

In at least one example, a method of positioning an atrial pacing lead for delivery of a cardiac pacing therapy comprises: sensing electrical activity of tissue of a patient from a plurality of external electrodes; determining a distribution of bi-atrial activation in response to the sensed electrical activity; determining a change in bi-atrial dyssynchrony in response to the determined distribution of bi-atrial activation; adjusting a target site for delivering the atrial pacing therapy in response to the determined change in bi-atrial dyssynchrony; and determining placement of the atrial pacing lead for delivery of the atrial pacing therapy in response to the adjusting.

In another example, a method of placing an atrial pacing lead for delivery of a cardiac pacing therapy comprises: performing at least one of positioning a single lead at a position adjacent the Bachman's Bundle, positioning a single lead within the right atrium, positioning a single lead within the left atrium, positioning a single lead at the atrial septum, and positioning both a single lead within the right atrium and a single lead within the left atrium; delivering an atrial pacing therapy in response to the performed positioning; sensing electrical activity of tissue of a patient from a plurality of external electrodes in response to the delivered atrial pacing therapy; determining a distribution of bi-atrial activation in response to the sensed electrical activity; determining whether there is a desired change in bi-atrial dyssynchrony in response to the determined distribution of bi-atrial activation; determining whether a lead placement end-point has been reached; and determining a target site for delivering the atrial pacing therapy in response to the lead placement end-point being reached.

In another example, a system for determining positioning of an atrial pacing lead for delivery of a cardiac pacing therapy comprises: a plurality of external electrodes to sense electrical activity of tissue of a patient from; and a computing apparatus configured to determine a distribution of bi-atrial activation in response to the sensed electrical activity, determine a change in bi-atrial dyssynchrony in response to the determined distribution of bi-atrial activation, adjust a target site for delivering the atrial pacing therapy in response to the determined change in bi-atrial dyssynchrony, and determine placement of an atrial pacing lead for delivery of the atrial pacing therapy in response to the adjusting.

In another example, a system for determining positioning of an atrial pacing lead for delivery of a cardiac pacing therapy comprises: one or more pacing electrodes to deliver an atrial pacing therapy in response to performing at least one of positioning a single lead at a position adjacent the Bachman's Bundle, positioning a single lead within the right atrium, positioning a single lead within the left atrium, positioning a single lead at the atrial septum, and positioning both a single lead within the right atrium and a single lead within the left atrium; a plurality of external electrodes to sense electrical activity of tissue of a patient in response to the delivered atrial pacing therapy; and a computing apparatus configured to determine a distribution of bi-atrial activation in response to the sensed electrical activity, determine whether there is a desired change in bi-atrial dyssynchrony in response to the determined distribution of bi-atrial activation, determine whether a lead placement end-point has been reached, and determine a target site for delivering the atrial pacing therapy in response to the lead placement end-point being reached.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
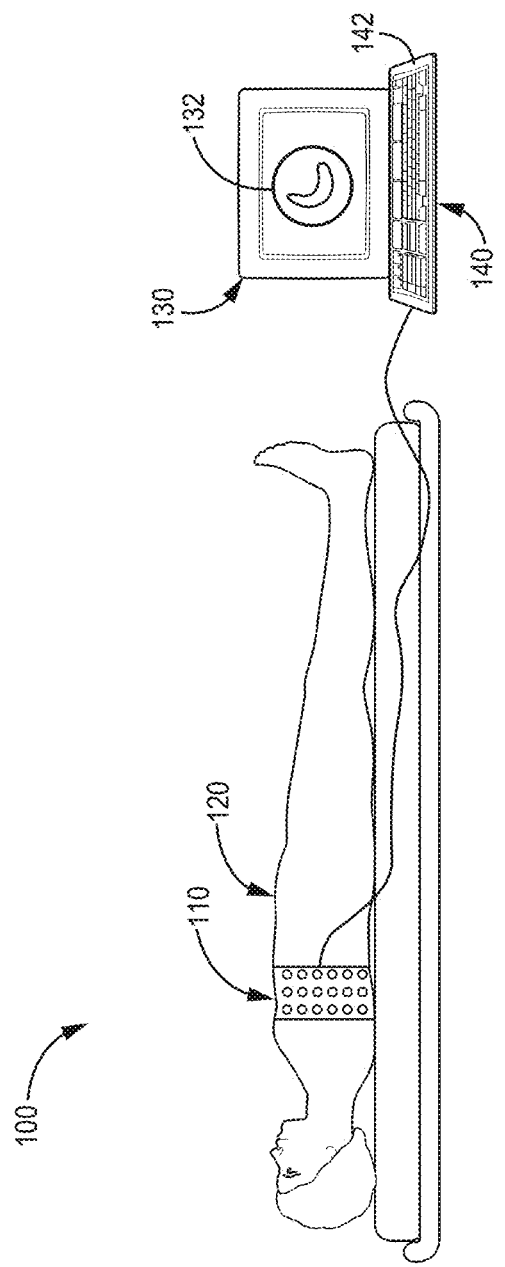
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-9. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Various exemplary systems, methods, and interfaces described herein may be configured to use electrode apparatus including external electrodes, display apparatus, and computing apparatus to noninvasively assist a user (e.g., a physician) in the evaluation of a patient's condition and/or atrial dyssynchrony pacing cardiac therapy being performed on, or delivered to, a patient. Patients with atrial dyssynchrony have wide P-waves and slower atrial conduction which may result in delayed atrial kick and lessened contribution of atrial kick to filling which can compromise ventricular function (heart failure). Atrial dyssynchrony may also be a cause for atrial arrhythmias and atrial fibrillation.

Atrial pacing therapy like targeting Bachmann's bundle for synchronized atrial activation or other means of multi-site atrial stimulation may help restore atrial synchrony and lead to better outcomes in these patients including bettering heart failure symptoms and potentially reducing burden of atrial arrhythmias. One limitation is finding a desired location or locations from to deliver pacing therapy within the atrium that results in a desired improvement of bi-atrial synchrony.

Methods are disclosed which includes application of multiple body-surface electrodes (ECG belt) on the patient and processing of P-waves based on signals received from the electrodes to derive atrial activation maps, compute metrics reflective of spatial electrical dyssynchrony of the atrium which can be used to assess the native atrial dyssynchrony and assess improvements in biatrial synchrony during pacing at different atrial sites. The target site on the atria may be the Bachmann's bundle or may be other sites in the left or right atrium or atrial septum. The end-point of the atrial lead placement procedure may be defined when fast spread of atrial activation is observed during procedure from the maps with a standard-deviation of activation times below a certain threshold.

FIG. 1 is a schematic diagram of a system for determining positioning of an atrial pacing lead for delivery of a cardiac pacing therapy according to the present disclosure. An exemplary system 100 including electrode apparatus 110, display apparatus 130, and computing apparatus 140 is depicted in FIG. 1. The electrode apparatus 110 as shown includes a plurality of electrodes incorporated, or included, within a band wrapped around the chest, or torso, of a patient 120. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

The display apparatus 130 and the computing apparatus 140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating a pacing location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
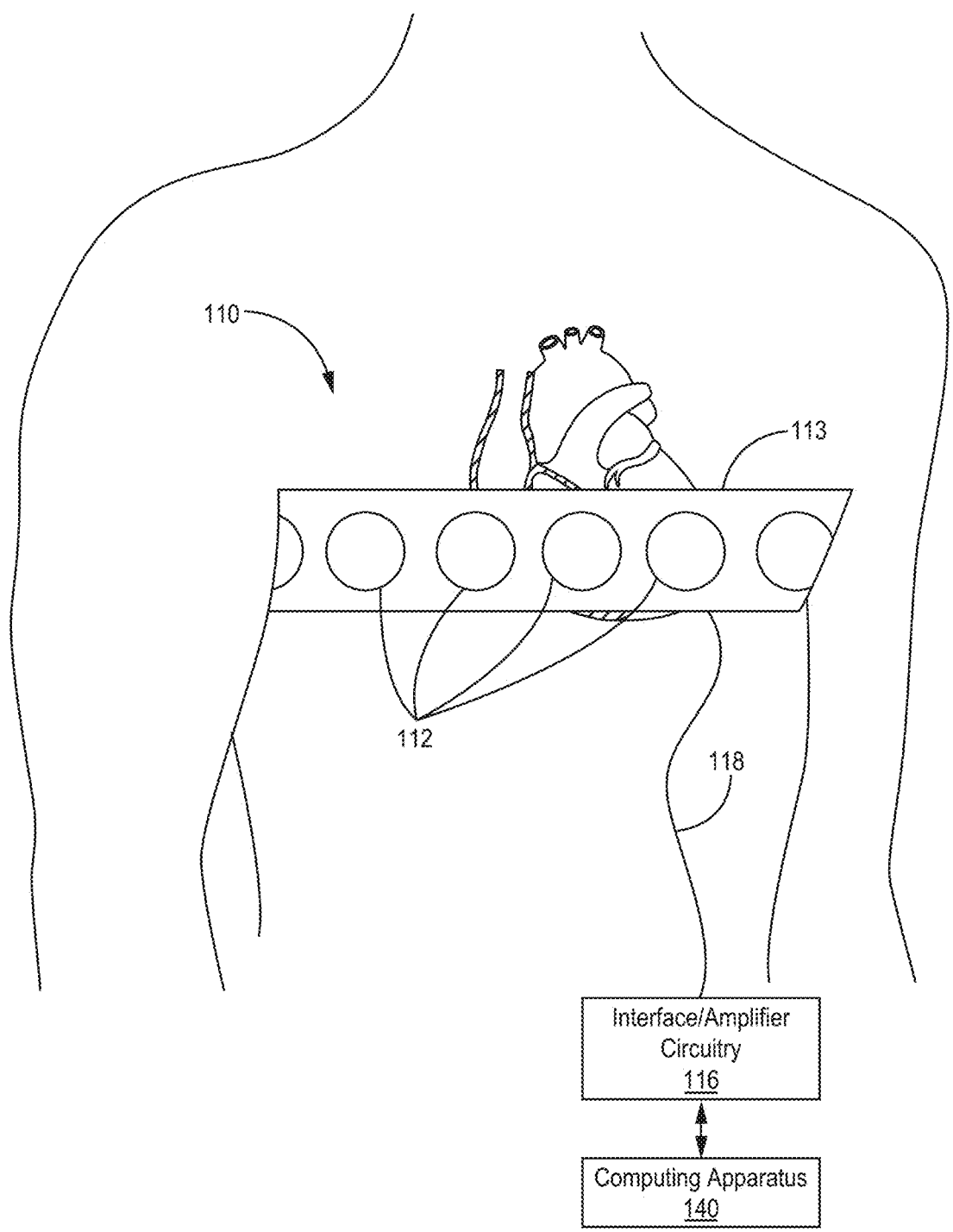
FIGS. 2-3 are diagrams of exemplary external electrode apparatus for measuring torso-surface potentials.

Electrical activation times of the patient's heart may be useful to evaluate a patient's cardiac condition and/or His bundle cardiac therapy being delivered to a patient. Surrogate electrical activation information or data of one or more regions of a patient's heart may be monitored, or determined, using electrode apparatus 110 as shown in FIG. 1 and in FIG. 2-3. The exemplary electrode apparatus 110 may be configured to measure body-surface potentials of a patient 120 and, more particularly, torso-surface potentials of a patient 120. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 120 such that the electrodes 112 surround the patient's heart. As further illustrated, the electrodes 112 may be positioned around the circumference of a patient 120, including the posterior, lateral, posterolateral, anterolateral, and anterior locations of the torso of a patient 120.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 120. Further, in other examples, electrodes 112 (e.g., arranged in an array) may be part of, or located within, patches, vests, and/or other manners of securing the electrodes 112 to the torso of the patient 120.

The electrodes 112 may be configured to surround the heart of the patient 120 and record, or monitor, the electrical signals associated with the depolarization and repolarization of the heart after the signals have propagated through the torso of a patient 120. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a patient's cardiac condition and/or His bundle pacing therapy being delivered to the patient.

Figure 3:
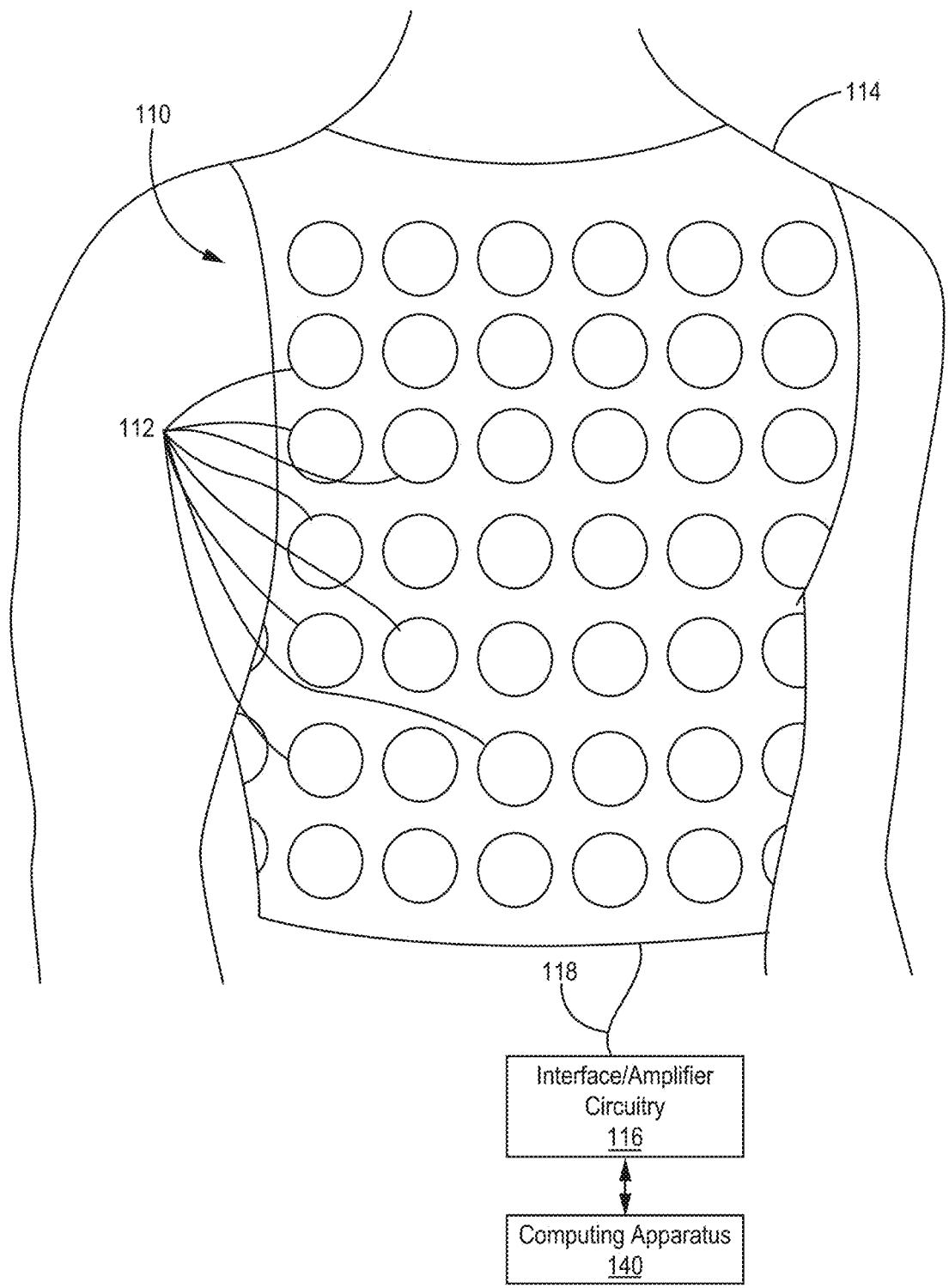

FIG. 3 illustrates another exemplary electrode apparatus 110 that includes a plurality of electrodes 112 configured to surround the heart of the patient 120 and record, or monitor, the electrical signals associated with the depolarization and repolarization of the heart after the signals have propagated through the torso of the patient 120. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 120, including, for example, the anterior, lateral, posterolateral, anterolateral, and posterior surfaces of the torso of the patient 120.

The vest 114 may be formed of fabric with the electrodes 112 attached to the fabric. The vest 114 may be configured to maintain the position and spacing of electrodes 112 on the torso of the patient 120. Further, the vest 114 may be marked to assist in determining the location of the electrodes 112 on the surface of the torso of the patient 120. In one or more embodiments, the vest 114 may include 17 or more anterior electrodes positionable proximate the anterior torso of the patient, and 39 or more posterior electrodes positionable proximate the anterior torso of the patient. In some examples, there may be about 25 electrodes 112 to about 256 electrodes 112 distributed around the torso of the patient 120, though other configurations may have more or less electrodes 112.

Figure 4:
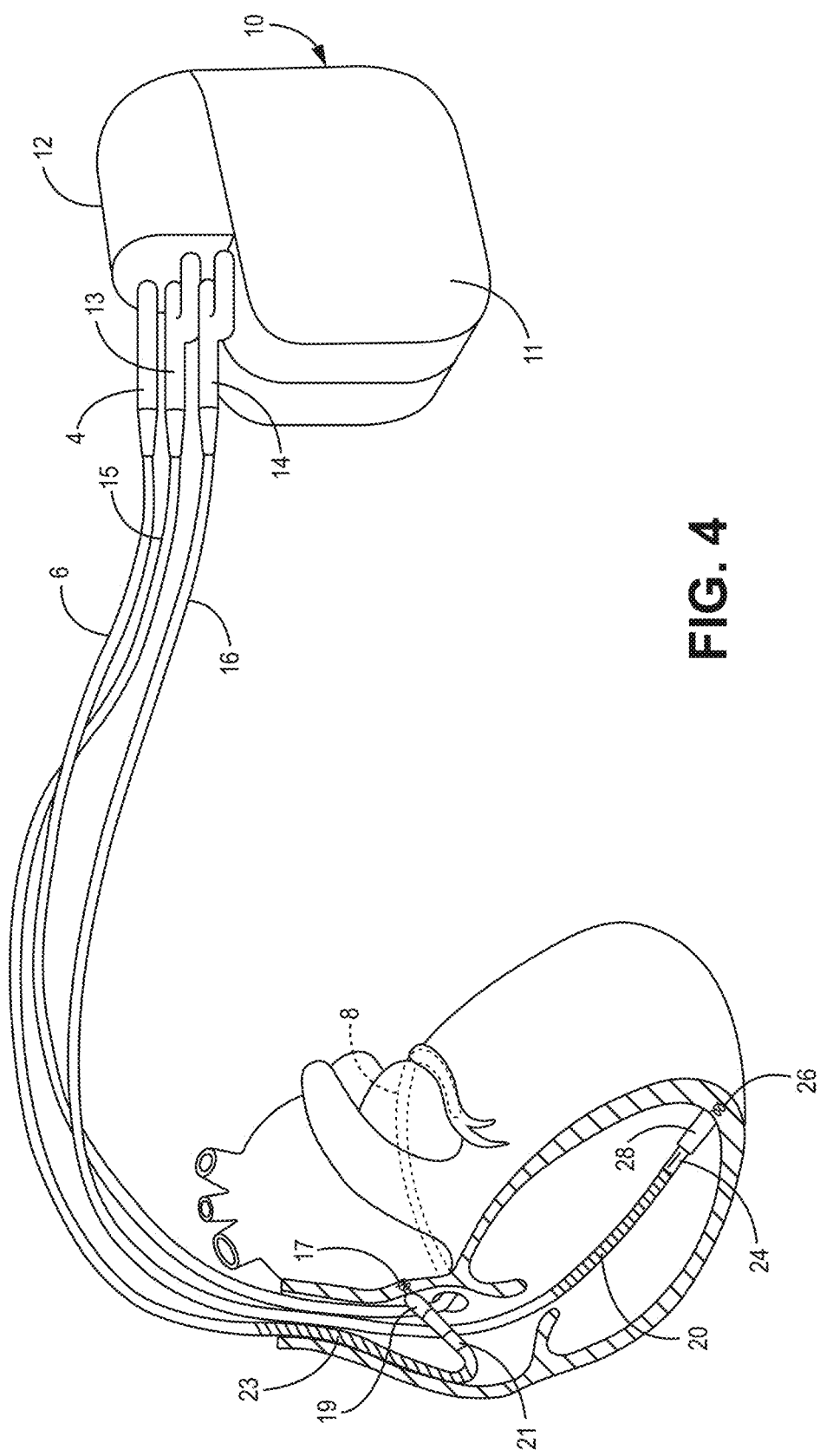
FIG. 4 is a schematic diagram of an exemplary medical device for detecting an arrhythmia according to an embodiment of the present disclosure.

FIG. 4 is a schematic diagram of an exemplary medical device for detecting an arrhythmia according to an embodiment of the present disclosure. As illustrated in FIG. 4, a medical device according to an embodiment of the present disclosure may be in the form of an implantable cardioverter defibrillator (ICD) 10 a connector block 12 that receives the proximal ends of a right ventricular lead 16, a right atrial lead 15 and a coronary sinus lead 6, used for positioning electrodes for sensing and stimulation in three or four heart chambers. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10. It is understood that although the device illustrated in FIG. 1 is a dual chamber device, other devices such as single chamber devices may be utilized to perform the technique of the present disclosure described herein.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 4 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4. The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 4. While a particular multi-chamber ICD and lead system is illustrated in FIG. 4, methodologies included in the present invention may adapted for use with any single chamber, dual chamber, or multi-chamber ICD or pacemaker system, subcutaneous implantable device, or other internal or external cardiac monitoring device.

ICD 10 may alternatively be configured as a subcutaneous device having sensing or pacing electrodes incorporated on the housing 11 of the device in which case transvenous leads are not required. A subcutaneous device may be coupled to a lead tunneled subcutaneously or submuscularly for delivering transthoracic pacing pulses and/or sensing ECG signals. An exemplary subcutaneous device is described in commonly assigned U.S. patent application Ser. Nos. 14/604,111 and 14/604,260. The techniques described herein can also be implemented in an external device, e.g. including patch electrodes and optionally another physiological sensor if desired, that can sense variable parameters as described herein.

Figure 5:
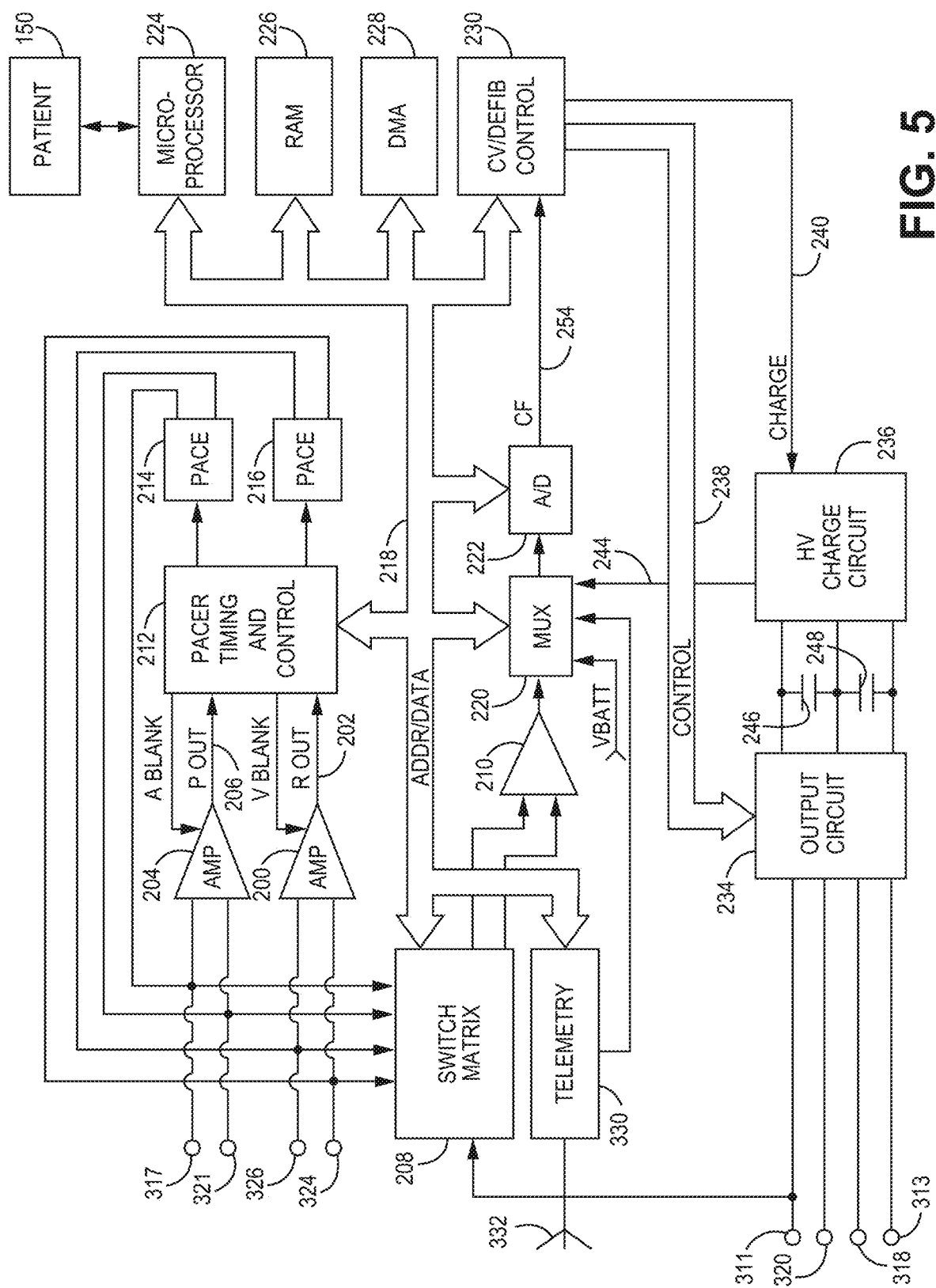
FIG. 5 is a functional schematic diagram of the medical device of FIG. 4.

FIG. 5 is a functional schematic diagram of the medical device of FIG. 4. This diagram should be taken as exemplary of the type of device with which the invention may be embodied and not as limiting. The disclosed embodiment shown in FIG. 5 is a microprocessor-controlled device, but the methods of the present invention may also be practiced with other types of devices such as those employing dedicated digital circuitry.

With regard to the electrode system illustrated in FIG. 4, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 313, and 318 provide electrical connection to coil electrodes 20, 8 and 23 respectively. Each of these connection terminals 311, 320, 313, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212.

Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. The blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy. Annotation of sensed events, which may be displayed and stored with EGM data, is described in U.S. Pat. No. 4,374,382 issued to Markowitz.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 5 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al.

As described herein, the electrode apparatus 110 may be configured to measure electrical information (e.g., electrical signals) representing different regions of a patient's heart.

For example, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces may be used to provide noninvasive assistance to a user in the evaluation and of a patient's cardiac health or status, and/or the evaluation of delivery of cardiac therapy such as atrial pacing therapy by use of the electrode apparatus 110 (e.g., cardiac therapy being presently-delivered to a patient during implantation or after implantation).

Patients with atrial dyssynchrony may experience wide P-waves and slower atrial conduction, which may result in delayed atrial kick and a reduction in the contribution of atrial kick to filling of the heart, which can compromise ventricular function (heart failure). Atrial dyssynchrony may also be a cause for atrial arrhythmias and atrial fibrillation. Atrial pacing therapy may be utilized to help restore atrial synchrony and lead to better outcomes in these patients including reducing heart failure symptoms and potentially reducing burden of atrial arrhythmias. In the heart's conduction system, Bachmann's bundle (also called the Bachmann bundle or the interatrial tract) is a branch of the anterior internodal tract that resides on the inner wall of the left atrium and is a broad band of cardiac muscle that passes from the right atrium, between the superior vena cava and the ascending aorta. Bachmann's bundle is considered the preferential path for electrical activation of the left atrium during normal sinus rhythm and is therefore considered to be part of the "atrial conduction system" of the heart. Therefore, atrial pacing using a single lead in the atrium that targets the Bachmann's bundle for synchronized atrial activation may be used to treat atrial dyssynchrony. Another possible pacing therapy for treating atrial dyssynchrony may include multi-site atrial stimulation using two leads, one positioned in the right atrium and the other being positioned within the left atrium, One limitation to the use of such pacing therapy to address atrial dyssynchrony is in finding a desired location or locations for delivering the pacing therapy from within either one of the atria, such as during Bachman's bundle pacing, or both of the atria, such as during bi-atrial pacing, that results in overall improvement of bi-atrial synchrony. According to the present disclosure, methods are disclosed which includes application of multiple body-surface electrodes (ECG belt) on the patient and processing of P-waves from those electrodes to derive atrial activation maps and compute metrics reflective of spatial electrical dyssynchrony of the atrium which can be used to assess the native atrial dyssynchrony and assess improvements in bi-atrial synchrony during pacing at different atrial sites. The target site on the atria may be the Bachmann's bundle or it could be other sites in the left or right atrium. The end-point of the atrial lead placement procedure may be defined when fast spread of atrial activation is observed from the atrial activation maps generated from the ECG belt. For example, the end-point of the atrial lead placement procedure may be defined when metrics reflective of spatial electrical dyssynchrony of the atrium, such as a standard-deviation of activation times, for example, are determined to be within a certain threshold or below a certain threshold.

Figure 6:
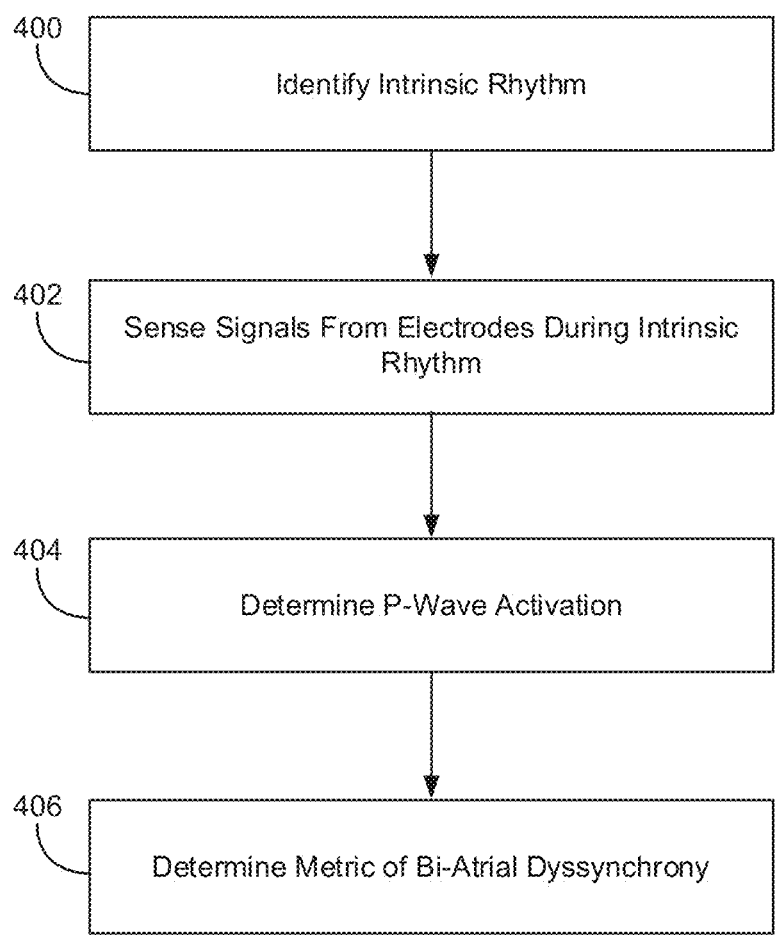
FIG. 6 is a flowchart of a method of determining a metric of bi-atrial dyssynchrony for use in the evaluation of atrial lead placement according to an example of the present disclosure.

FIG. 6 is a flowchart of a method of determining a metric of bi-atrial dyssynchrony for use in the evaluation of atrial lead placement according to an example of the present disclosure. As illustrated in FIG. 6, in order to evaluate atrial lead placement for delivery of atrial pacing therapy, while the electrode apparatus 110 is worn by the patient, the computing apparatus 140 identifies the occurrence of an intrinsic rhythm, Block 400, using display apparatus 130 for example, and processes signals sensed from each of the external electrodes 112 during the intrinsic rhythm, Block 402. The computing apparatus 140 determines a P-wave activation of the intrinsic rhythm based on the signals sensed via each of the external electrodes 112, Block 404. Rather than determining the P-wave activation within a single atrial chamber, the computing apparatus 140 determines a P-wave activation signal across both the left and the right atrium of the heart, i.e., bi-atrial activation, Block 404. The computing apparatus 140 then determines a metric of bi-atrial dyssnchrony based on the determined intrinsic P-wave, Block 406.

Figure 7:
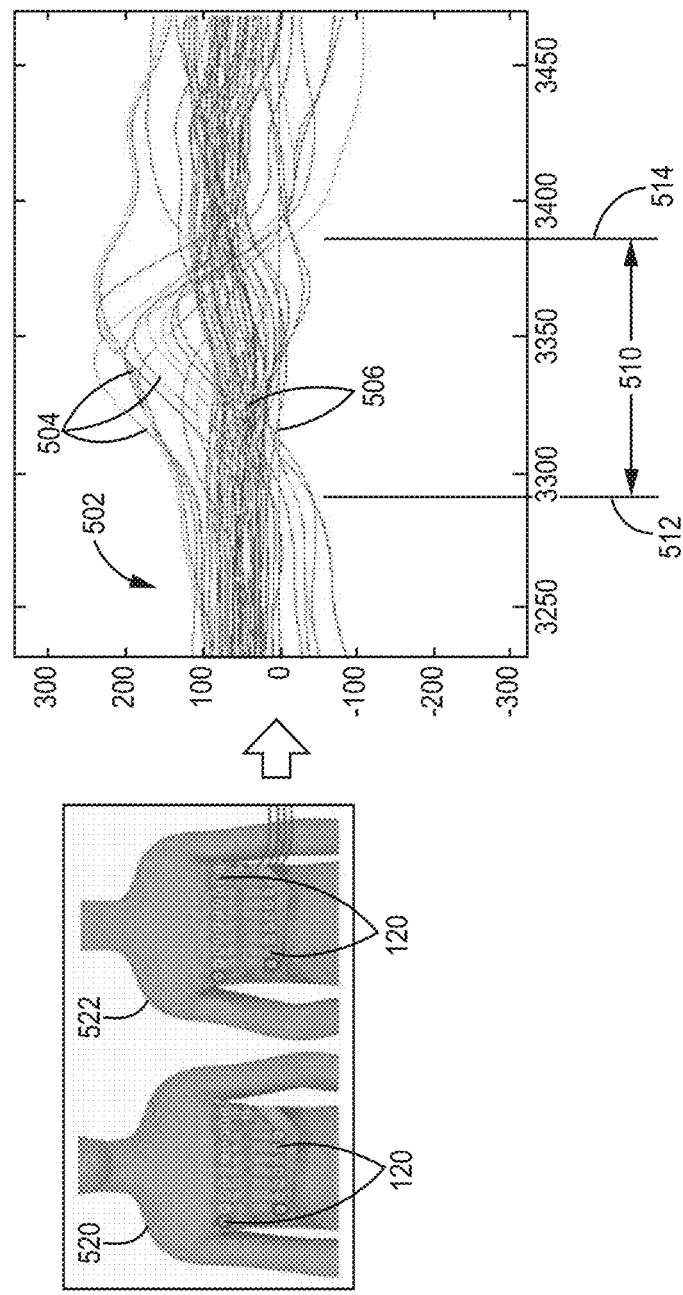
FIG. 7 is a schematic diagram illustrating determination of P-wave activation according to an example of the present disclosure.

FIG. 7 is a schematic diagram illustrating determination of P-wave activation according to an example of the present disclosure. In one example, the metric of bi-atrial dyssynchrony determined in Block 406 may be based on determining a standard deviation of activation times for a given determined P-wave. For example, as illustrated in FIG. 7, during the determination of a P-wave activation, Block 404 of FIG. 6, the computing apparatus 140 determines a P-wave window 500 of signals 502 sensed from each of the multiple electrodes 112 based on the change in amplitude of the signals 502, for example.

As illustrated in FIG. 7, prior to the P-wave window 500, the sensed signals 502 are all relatively flat, indicating the P-wave is not being detected. During detection of the P-wave activation, the amplitude of certain signals 504 from corresponding electrodes 112 tends to increase, while the amplitude of other signals 506 tend to remain the same. Therefore, according to one example of the present disclosure, the computing apparatus 140 senses the ECG signals 502 from each of the electrodes 112 and determines whether there is an increase in amplitude of a predetermined number of the sensed signals 502. A P-wave window 510 is defined as having a start point 512 that is determined to occur once there is an increase in amplitude for a predetermined number of the sensed signals 502, and having an endpoint 514 that is determined to occur once there is a decrease in amplitude for a predetermined number of the sensed signals 502.

The P-wave activation time at each electrode is determined based on the interval between the start of the window and a fiducial point of the P-wave signal sensed at that particular electrode within this time window. The fiducial point may be the point corresponding to the steepest negative slope of the P-wave signal. A surface isochronal map of electrical activation of the atrium is generated based on the activation times of the sensed signals 502 sensed during the P-wave window 510. Electrical heterogeneity information generated from the surface isochronal map is then used to determine a distribution of atrial activation, enabling a metric of bi-atrial dyssynchrony to be determined, Block 406, in response to the determined distribution of atrial activation, described below.

Figure 8:
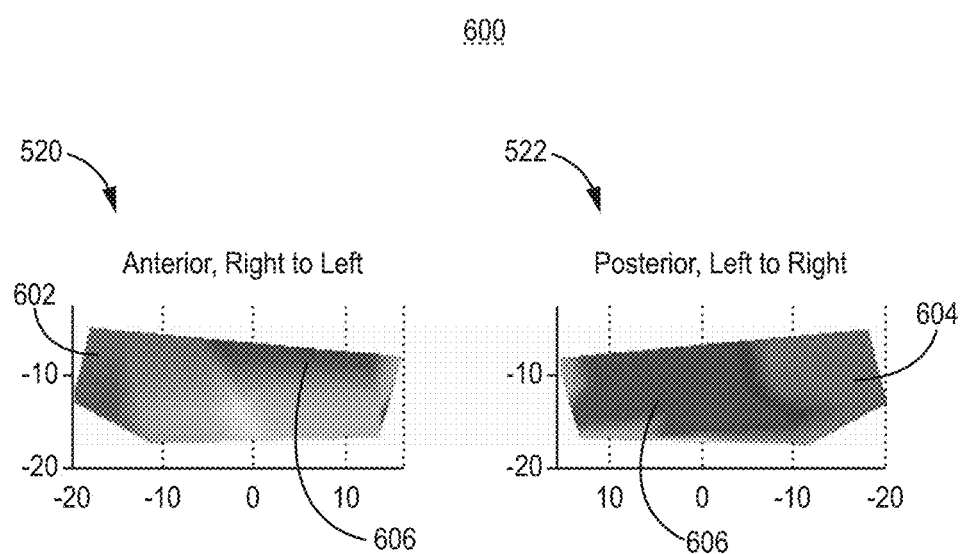
FIG. 8 is an exemplary illustration of generation of distribution of atrial activation information according to an example of the present disclosure.

FIG. 8 is an exemplary illustration of generation of distribution of atrial activation information according to an example of the present disclosure. As illustrated in FIG. 8, the computing apparatus 140 generates isochronal maps 600 depicting the distribution of bi-atrial activation times on the anterior and posterior aspects of the patient's torso during atrial depolarization based on the electrical activation occurring within the determined P-wave time window 510. The isochronal maps 600 illustrate an activation spread 602 from right to left across electrodes 112 positioned along an anterior side 520 (shown also in FIG. 7) of the patient, and an activation spread 604 from right to left across electrodes 112 along a posterior side 522 (shown also in FIG. 7) of the patient.

An activation delay 606, which results in longer or slower conduction time, is indicated by the occurrence of darker portions of the activations spreads 602 and 604. In the example illustrated in FIG. 8, the activation spread 604 along the posterior side 522 of the patient includes a larger darker portion indicative of a larger activation delay 606 relative to the activation delay 606 for the activation spread 602 along the anterior side 520. As a result, an atrial dyssynchrony score would be indicated by the deviation between the activation delay 606 associated with the activation spread 602 along the anterior side 520 and the activation spread 604 along the posterior side 522, resulting in a dyssynchrony score.

For example, assuming the P-wave activation times from twenty electrodes associated with the isochronal map of the anterior side 520 are 10 ms, 10 ms, 12 ms, 14 ms, 16 ms, 18 ms, 20 ms, 24 ms, 25 ms, 27 ms, 31 ms, 34 ms, 37 ms, 38 ms, 40 ms, 41 ms, 42 ms, 44 ms, 45 ms, and 5 ms, and the activation times of twenty electrodes associated with the isochronal map of the posterior side 522 are 67 ms, 72 ms, 77 ms, 81 ms, 81 ms, 100 ms, 105 ms, 112 ms, 115 ms, 120 ms, 120 ms, 121 ms, 76 ms, 21 ms, 22 ms, 18 ms, 19 ms, 19 ms, 18 ms, and 18 ms, the metric of bi-atrial dyssynchrony determined in Block 406 of FIG. 6 for the determined intrinsic P-wave is determined to be a standard deviation of the anterior and posterior P-wave activation times combined together, which in this particular example is 36 ms. The determined metric of bi-atrial dyssynchrony during intrinsic rhythm, i.e., 36 ms, is stored by the computing apparatus 140. In another embodiment, the metric of bi-atrial dyssynchrony may be based on difference between the average anterior P wave activation times and average posterior P-wave activation times. Other statistical measures of heterogeneity and dispersion may be applied to the set of anterior and posterior P-wave activation times to generate metrics of bi-atrial dyssynchrony.

Figure 9:
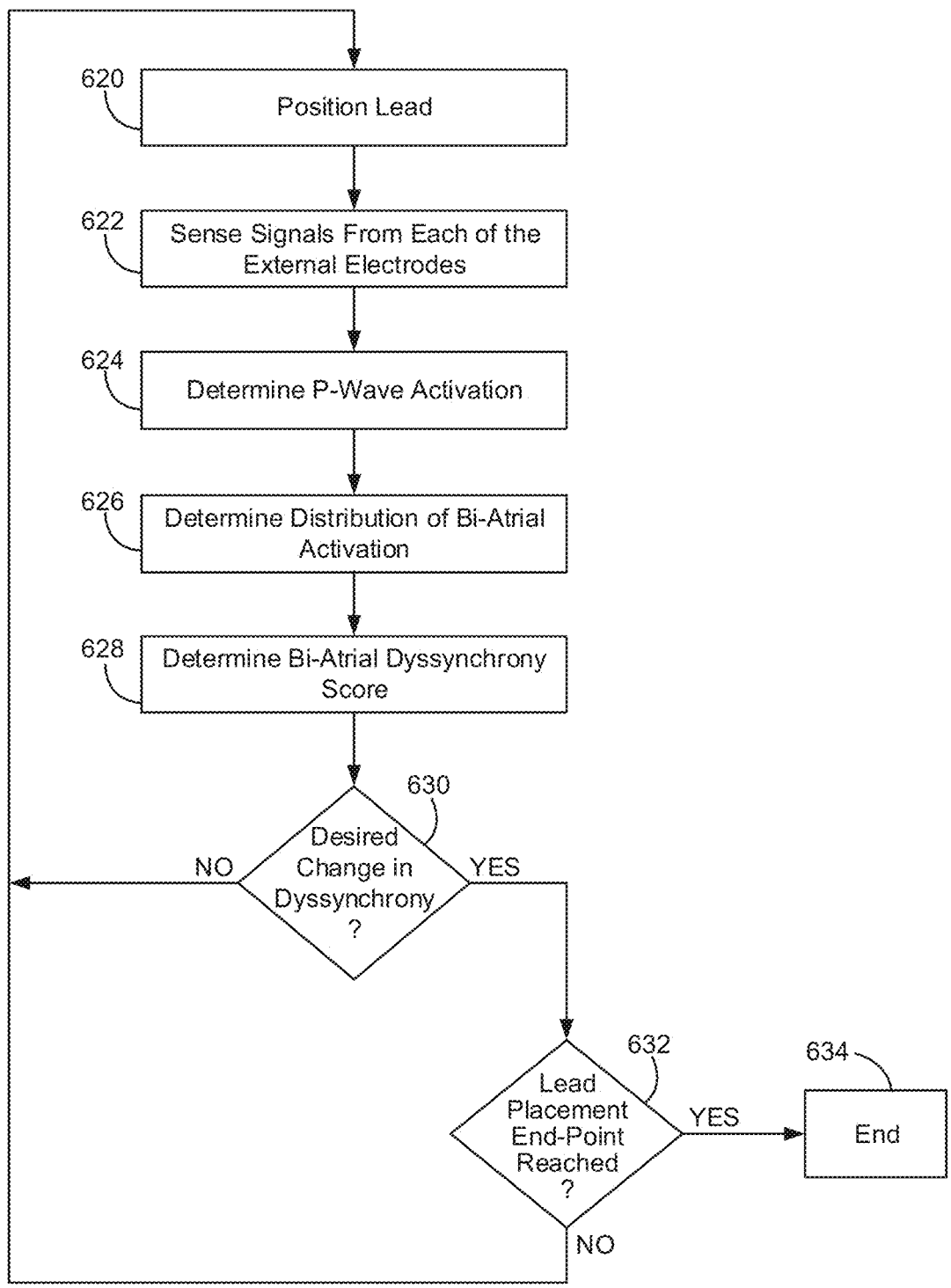
FIG. 9 is a flowchart of a method of determining atrial lead placement for delivering an atrial pacing therapy according to an example of the present disclosure.

FIG. 9 is a flowchart of a method of determining atrial lead placement for delivering an atrial pacing therapy according to an example of the present disclosure. According to one example of the present disclosure, once the metric of bi-atrial dyssynchrony during intrinsic rhythm is determined, Block 406 of FIG. 6, as described above, placement of one or more leads in one or both of the atrial chambers for delivering atrial pacing therapy is performed using the multiple body-surface electrodes of the electrode apparatus (ECG belt) 110 positioned on the patient, described above. For example, as illustrated in FIG. 9, the lead placement may start with one or more leads being positioned at one or more target sites, Block 620, such as a single lead being positioned within the vicinity of or adjacent the Bachman's Bundle, for example, a single lead being positioned at another location within either the right atrium or the left atrium, or using two leads, with one lead positioned within the right atrium and the second lead positioned within the left atrium. During subsequent delivery of the atrial pacing therapy, electrical activation information associated with the patient's heart is sensed, using the external electrodes 112 of the electrode apparatus 110, described above, and the computing apparatus 140 determines a P-wave activation, Block 624, for the current lead position based on signals sensed via each of the external electrodes 112, Block 622, as described above. In the same way as during the intrinsic atrial rhythm described above, rather than determining the P-wave activation within a single atrial chamber, the computing apparatus 140 determines a P-wave activation signal across both the left and the right atrium of the heart, i.e., bi-atrial activation, Block 624, during subsequent placement of one or more leads.

Once the P-wave activation has been determined, Block 624, the computing apparatus 140 then determines the distribution of atrial activation, Block 626, based on the determined P-wave activation, Block 624, and determines an atrial dyssynchrony score associated with the current position of the one or more leads, Block 628. Based on the determined atrial dyssynchrony score, Block 628, the computing apparatus 140 determines whether the current atrial dyssynchrony score results in a predetermined reduction in atrial dyssynchrony, Block 630. If the current atrial dyssynchrony score does not result in a reduction in atrial dyssynchrony, No in Block 630, the single lead, or one or both of the two leads are repositioned, Block 620, and the process is repeated for the lead or leads while in the adjusted position.

If the current atrial dyssynchrony score results in a reduction in atrial dyssynchrony, Yes in Block 630, the computing apparatus 140 determines whether a lead-placement endpoint has been reached, Block 632. If it is determined that a lead-placement endpoint has not been reached, No in Block 632, the single lead, or one or both of the two leads are repositioned, Block 620, and the process is repeated for the lead or leads while in the adjusted position. If it is determined that a lead-placement endpoint has been reached, Yes in Block 632, the current lead position is determined to be satisfactory for delivery of atrial dyssynchrony pacing, Block 634.

During the determination as to whether the current atrial dyssynchrony score results in a desired change in atrial dyssynchrony, Block 630, the computing apparatus 140 determines whether the atrial dyssynchrony score for the current placement of the one or more leads results in a predetermined reduction in dyssynchrony. For example, if the metric of bi-atrial dyssnchrony determined during the intrinsic rhythm is 36 ms, the computing apparatus determines whether the current bi-atrial dyssynchrony score, Block 628, correspond to, i.e., results in a predetermined percentage reduction in the intrinsic bi-atrial dyssnchrony, Block 630. In one example, the predetermined percentage may be between a 15 percent and a 20 percent reduction in bi-atrial dyssynchrony, i.e., a 20 percent reduction in the intrinsic rhythm bi-atrial dyssnchrony score of 36 ms, for example. Therefore, if a 20 percent reduction is determined to occur, Yes in Block 630, the lead placement end-point is determined to have been reached, Yes in Block 632. On the other hand, if a 20 percent reduction is not determined to occur, No in Block 630, the lead placement end-point is not determined to have been reached, No in Block 632, and the lead placement is adjusted, Block 620 and the process is repeated for the adjusted lead placement.

In another embodiment, during the determination of whether the lead placement end-point has been reached, Block 632, for placement of a single lead in the vicinity of the Bachman's Bundle, once the position of the lead in the vicinity of the Bachman's Bundle results in the desired change in bi-atrial dyssynchrony, Yes in Block 632, the process may continue by determining positioning of another lead configuration. For example, the computing apparatus 140 may determine a bi-atrial dyssynchrony score for positioning of a single lead in one of the right atrium or the left atrium, or for positioning both a single lead in the right atrium and a single lead within the left atrium and repeating the process for that lead placement.

Once the bi-atrial dyssynchrony score is determined for the single lead positioned in the right atrium or in the left atrium, or for the two single leads, one positioned in the right atrium and the second positioned in the left atrium, the computing device 140 determines whether there is a desired change in bi-atrial dyssynchrony, Block 360, and the process is repeated until the positioning of the lead or leads results in the desired change in bi-trial dyssynchrony, Yes in Block 630. This determined change in bi-atrial dyssynchrony is then compared with the change in bi-atrial dyssynchrony that was determined for the lead positioned within the vicinity of the Bachman's Bundle. A determination is then made as to which lead placement results in the greatest change in bi-atrial dyssynchrony. For example, if the desired change in bi-atrial dyssynchrony, Block 630, determined for the lead positioned within the vicinity of the Bachman's Bundle is greater than the desired change in bi-atrial dyssynchrony, Block 630, determined for the single lead positioned in the right atrium or in the left atrium, or for the two single leads, one positioned in the right atrium and the second positioned in the left atrium, the lead being positioned within the vicinity of the Bachman's Bundle is chosen as the lead end-point and utilized to deliver the atrial pacing therapy, and vice versa.

In another embodiment, during the determination of whether the lead placement end-point has been reached, Block 632, in an example of placement of a single lead in the vicinity of the Bachman's Bundle, if the determination of there being a desired change in bi-atrial dyssynchrony, Block 630, is not satisfied for a predetermined number of attempts at positioning the lead, the computing apparatus 140 may generate an alert to indicate failure of the lead placement within the vicinity of the Bachman's Bundle, and the process is repeated using an alternate lead placement, such as single lead positioned in either the right atrium or in the left atrium, or the use of two single leads, one positioned in the right atrium and the second positioned in the left atrium. The predetermined number of attempts may be 5 attempts, 10 attempts, 15 attempts, or 20 attempts, for example.

In this way, the computing apparatus 140 is able to determine which lead placement configuration results in the greatest change in dyssynchrony and choose that lead placement configuration for placement of one or more atrial leads. It is understood that the computing apparatus 140 may also make such a determination between any number of the possible lead placement configurations. For example, a determination may be made between the single lead positioned within the vicinity of the Bachman's Bundle and a single lead positioned in one of the left atrium and the right atrium or atrial septum, between a both single lead positioned in the right atrium and a single lead positioned in the left atrium, and between both a single lead positioned in the right atrium and a single lead positioned within the left atrium and a single lead positioned in one of the left atrium and the right atrium, and so on.

As a result, the present disclosure enables correction of atrial dyssynchrony using any one of a number of different lead placement applications to assist in enabling a more targeted atrial lead placement. In addition, such an lead placement may have a number of different applications including diastolic heart failure, systolic heart failure, and patients experiencing atrial fibrillation. In addition, the information may be used in a real-time procedure to help targeted atrial placement, especially for engaging electrical activation across the whole atrial conduction system. In the post-implant setting, the atrial activation maps and metrics of biatrial synchrony may be used for management of atrial dyssynchrony which may include titration of device parameters like pacing outputs, pacing rate, pacing vector, and timing between sequential pacing pulses if more than one pacing lead are involved.

The exemplary systems, methods, and graphical user interfaces described herein may be used with respect to the implantation and configuration of an implantable medical device (IMD) and/or one or more leads configured to be located proximate one or more portions of a patient's heart, e.g., proximate the His bundle).

The techniques described in this disclosure, including those attributed to the ICD 10, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

ILLUSTRATIVE EMBODIMENTS

Embodiment 1

A method of positioning an atrial pacing lead for delivery of a cardiac pacing therapy, comprising:
sensing electrical activity of tissue of a patient from a plurality of external electrodes;

determining a distribution of bi-atrial activation in response to the sensed electrical activity;
determining a change in bi-atrial dyssynchrony in response to the determined distribution of bi-atrial activation;
adjusting a target site for delivering the atrial pacing therapy in response to the determined change in bi-atrial dyssynchrony; and
determining placement of the atrial pacing lead for delivery of the atrial pacing therapy in response to the adjusting.

Embodiment 2

The method of embodiment 1, further comprising:
determining an increase in amplitude of the sensed electrical activity for a predetermined number of the plurality of electrodes;
determining a decrease in amplitude of the sensed electrical activity for a predetermined number of the plurality of electrodes;
generating electrical activation information from the sensed electrical activity within a window extending between the determined increase in amplitude and the determined decrease in amplitude; and
determining the distribution of bi-atrial activation and electrical heterogeneity in response to the electrical activation information.

Embodiment 3

The method of any of embodiments 1-2, further comprising:
determining a first set of activation times corresponding to a posterior set of electrodes from the sensed electrical activity within the window;
determining a second set of activation times corresponding to an anterior set of electrodes from the sensed electrical activity within the window;
determining a standard deviation of activation times for a combination of the first set of activation times and the second set of activation times; and
determining a bi-atrial dyssnchrony score in response to the determined standard deviation.

Embodiment 4

A method of placing an atrial pacing lead for delivery of a cardiac pacing therapy, comprising:
performing at least one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium;
delivering an atrial pacing therapy in response to the performed positioning;
sensing electrical activity of tissue of a patient from a plurality of external electrodes in response to the delivered atrial pacing therapy;
determining a distribution of bi-atrial activation in response to the sensed electrical activity;
determining whether there is a desired change in bi-atrial dyssynchrony in response to the determined distribution of bi-atrial activation;
determining whether a lead placement end-point has been reached; and
determining a target site for delivering the atrial pacing therapy in response to the lead placement end-point being reached.

Embodiment 5

The method of embodiment 4, further comprising:
comparing the determined distribution of bi-atrial activation to a distribution of bi-atrial activation for an intrinsic rhythm; and
determining whether there is a desired change in bi-atrial dyssynchrony in response to the comparing.

Embodiment 6

The method of and of embodiments 4-5, further comprising:
determining an increase in amplitude of the sensed electrical activity for a predetermined number of the plurality of electrodes;
determining a decrease in amplitude of the sensed electrical activity for a predetermined number of the plurality of electrodes;
generating electrical heterogeneity information of the sensed electrical activity within a window extending between the determined increase in amplitude and the determined decrease in amplitude; and
determining the distribution of bi-atrial activation in response to the electrical heterogeneity information.

Embodiment 7

The method of embodiment 6, further comprising:
determining a first set of activation times corresponding to a posterior set of electrodes from the sensed electrical activity within the window;
determining a second set of activation times corresponding to an anterior set of electrodes from the sensed electrical activity within the window;
determining a standard deviation of activation times for a combination of the first set of activation times and the second set of activation times; and
determining a bi-atrial dyssnchrony score in response to the determined standard deviation.

Embodiment 8

The method of embodiment 7, further comprising:
comparing the determined bi-atrial dyssynchrony score to an intrinsic rhythm bi-atrial dyssynchrony score;
determining whether the bi-atrial dyssynchrony score corresponds to a predetermined reduction in the intrinsic rhythm bi-atrial dyssynchrony score; and
determining the lead placement end-point has been reached in response to the bi-atrial dyssynchrony score corresponding to the predetermined reduction.

Embodiment 9

The method of any of embodiments 7-8, further comprising:
comparing the determined bi-atrial dyssynchrony score to an intrinsic rhythm bi-atrial dyssynchrony score;
determining a change in bi-atrial dyssynchrony in response to the comparing;

determining that there is the desired change in bi-atrial dyssynchrony in response to the determined change in bi-atrial dyssynchrony for two or more of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium; and determining the lead placement end-point has been reached in response to a comparing of the two or more determined changes in bi-atrial dyssynchrony associated with the determining that there is the desired change in bi-atrial dyssynchrony.

Embodiment 10

The method of any of embodiments 4-9, further comprising:
- determining that there is not the desired change in bi-atrial dyssynchrony for the current performing of at least one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium;
- determining whether there is the desired change in bi-atrial dyssynchrony for performing another one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium; and
- determining the lead placement end-point has been reached in response to there being the desired change in bi-atrial dyssynchrony for the other one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium.

Embodiment 11

A system for determining positioning of an atrial pacing lead for delivery of a cardiac pacing therapy, comprising:
- a plurality of external electrodes to sense electrical activity of tissue of a patient from; and
- a computing apparatus configured to determine a distribution of bi-atrial activation in response to the sensed electrical activity, determine a change in bi-atrial dyssynchrony in response to the determined distribution of bi-atrial activation, adjust a target site for delivering the atrial pacing therapy in response to the determined change in bi-atrial dyssynchrony, and determine placement of an atrial pacing lead for delivery of the atrial pacing therapy in response to the adjusting.

Embodiment 12

The system of embodiment 11, wherein the computing apparatus is configured to determine an increase in amplitude of the sensed electrical activity for a predetermined number of the plurality of electrodes, determine a decrease in amplitude of the sensed electrical activity for a predetermined number of the plurality of electrodes, generate electrical heterogeneity information of the sensed electrical activity within a window extending between the determined increase in amplitude and the determined decrease in amplitude; and determine the distribution of bi-atrial activation in response to the electrical heterogeneity information.

Embodiment 13

The system of any of embodiments 11-12, wherein the computing apparatus is configured to determine a first activation delay corresponding to a posterior activation spread of the sensed electrical activity within the window. determine a second activation delay corresponding to an anterior activation spread of the sensed electrical activity within the window, determine a deviation between the first activation delay and the second activation delay, and determine a bi-atrial dyssnchrony score in response to the determined deviation.

Embodiment 14

A system for determining positioning of an atrial pacing lead for delivery of a cardiac pacing therapy, comprising:
- one or more pacing electrodes to deliver an atrial pacing therapy in response to performing at least one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium;
- a plurality of external electrodes to sense electrical activity of tissue of a patient in response to the delivered atrial pacing therapy; and
- a computing apparatus configured to determine a distribution of bi-atrial activation in response to the sensed electrical activity, determine whether there is a desired change in bi-atrial dyssynchrony in response to the determined distribution of bi-atrial activation, determine whether a lead placement end-point has been reached, and determine a target site for delivering the atrial pacing therapy in response to the lead placement end-point being reached.

Embodiment 15

The system of embodiment 14, wherein the computing apparatus is configured to compare the determined distribution of bi-atrial activation to a distribution of bi-atrial activation for an intrinsic rhythm and determine whether there is a desired change in bi-atrial dyssynchrony in response to the comparing.

Embodiment 16

The system of any of embodiments 14-15, wherein the computing apparatus is configured to determine an increase in amplitude of the sensed electrical activity for a predetermined number of the plurality of electrodes, determine a decrease in amplitude of the sensed electrical activity for a predetermined number of the plurality of electrodes, generate electrical heterogeneity information of the sensed electrical activity within a window extending between the determined increase in amplitude and the determined decrease in amplitude, and determine the distribution of bi-atrial activation in response to the electrical heterogeneity information.

Embodiment 17

The system of any of embodiments 14-16, wherein the computing apparatus is configured to determine a first set of activation times corresponding to a posterior set of electrodes from the sensed electrical activity within the window, determine a second set of activation times corresponding to an anterior set of electrodes from the sensed electrical activity within the window, determine a standard deviation of activation times for a combination of the first set of activation times and the second set of activation times, and determine a bi-atrial dyssnchrony score in response to the determined standard deviation.

Embodiment 18

The system of embodiment 17, wherein the computing apparatus is configured to compare the determined bi-atrial dyssynchrony score to an intrinsic rhythm bi-atrial dyssynchrony score, determine whether the bi-atrial dyssynchrony score corresponds to a predetermined reduction in the intrinsic rhythm bi-atrial dyssynchrony score, and determine the lead placement end-point has been reached in response to the bi-atrial dyssynchrony score corresponding to the predetermined reduction.

Embodiment 19

The system of any of embodiments 17-18, wherein the computing apparatus is configured to compare the determined bi-atrial dyssynchrony score to an intrinsic rhythm bi-atrial dyssynchrony score, determine a change in bi-atrial dyssynchrony in response to the comparing, determine that there is the desired change in bi-atrial dyssynchrony in response to the determined change in bi-atrial dyssynchrony for two or more of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium, and determine the lead placement end-point has been reached in response to a comparing of the two or more determined changes in bi-atrial dyssynchrony associated with the determining that there is the desired change in bi-atrial dyssynchrony.

Embodiment 20

The system of any of claims 14-19, wherein the computing apparatus is configured to determine that there is not the desired change in bi-atrial dyssynchrony for the current performing of at least one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium, determine whether there is the desired change in bi-atrial dyssynchrony for performing another one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium, and determine the lead placement end-point has been reached in response to there being the desired change in bi-atrial dyssynchrony for the other one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium.

What is claimed:

1. A method of positioning an atrial pacing lead for delivery of a cardiac pacing therapy, comprising:
    sensing electrical activity of tissue of a patient from a plurality of external electrodes;
    determining a distribution of bi-atrial activation based on the sensed electrical activity during delivery of atrial pacing therapy at one or more target sites; and
    determining acceptability of the atrial pacing therapy at the one or more target sites based on the distribution of bi-atrial activation.

2. The method of claim 1, wherein determining a distribution of bi-atrial activation comprises:
    determining an increase in amplitude of the sensed electrical activity for a predetermined number of the plurality of electrodes;
    determining a decrease in amplitude of the sensed electrical activity for a predetermined number of the plurality of electrodes;
    generating electrical heterogeneity information of the sensed electrical activity within a window extending between the determined increase in amplitude and the determined decrease in amplitude; and
    determining the distribution of bi-atrial activation based on the generated electrical heterogeneity information.

3. The method of claim 2, wherein generating electrical heterogeneity information comprises:
    determining a first set of activation times corresponding to a posterior set of electrodes from the sensed electrical activity within the window;
    determining a second set of activation times corresponding to an anterior set of electrodes from the sensed electrical activity within the window;
    determining a standard deviation of activation times for a combination of the first set of activation times and the second set of activation times; and
    determining a bi-atrial dyssynchrony score in response to the determined standard deviation.

4. A method of placing an atrial pacing lead for delivery of a cardiac pacing therapy, comprising:
    performing at least one of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium;
    delivering an atrial pacing therapy in response to the performed positioning;
    sensing electrical activity of tissue of a patient from a plurality of external electrodes in response to the delivered atrial pacing therapy;
    determining a distribution of bi-atrial activation in response to the sensed electrical activity; and
    determining a target site for delivering the atrial pacing therapy if a desired change in bi-atrial dyssynchrony occurs based on the distribution of bi-atrial activation.

5. The method of claim 4, wherein determining a distribution of bi-atrial activation in response to the sensed electrical activity comprises comparing the determined distribution of bi-atrial activation to a distribution of bi-atrial activation for an intrinsic rhythm.

6. The method of claim 4, wherein determining a distribution of bi-atrial activation in response to the sensed electrical activity comprises:
- determining an increase in amplitude of the sensed electrical activity for a predetermined number of the plurality of electrodes;
- determining a decrease in amplitude of the sensed electrical activity for a predetermined number of the plurality of electrodes;
- generating electrical heterogeneity information of the sensed electrical activity within a window extending between the determined increase in amplitude and the determined decrease in amplitude; and
- determining the distribution of bi-atrial activation based on the generated electrical heterogeneity information.

7. The method of claim 6, wherein generating electrical heterogeneity information comprises:
- determining a first set of activation times corresponding to a posterior set of electrodes from the sensed electrical activity within the window;
- determining a second set of activation times corresponding to an anterior set of electrodes from the sensed electrical activity within the window;
- determining a standard deviation of activation times for a combination of the first set of activation times and the second set of activation times; and
- determining a bi-atrial dyssynchrony score based on the determined standard deviation.

8. The method of claim 7, wherein determining a target site for delivering the atrial pacing therapy if a desired change in bi-atrial dyssynchrony occurs:
- determining whether the bi-atrial dyssynchrony score corresponds to a predetermined reduction in an intrinsic rhythm bi-atrial dyssynchrony score.

9. The method of claim 7, wherein determining a target site for delivering the atrial pacing therapy if a desired change in bi-atrial dyssynchrony occurs further comprises:
- comparing the determined bi-atrial dyssynchrony score to the intrinsic rhythm bi-atrial dyssynchrony score;
- determining a change in bi-atrial dyssynchrony in response to the comparing; and
- determining that there is the desired change in bi-atrial dyssynchrony in response to determination of a change in bi-atrial dyssynchrony for two or more of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium.

10. A system for determining positioning of an atrial pacing lead for delivery of a cardiac pacing therapy, comprising:
- a plurality of external electrodes to sense electrical activity of tissue of a patient; and
- a computing apparatus comprising processing circuitry and coupled to the electrode apparatus and configured to:
  - determine a distribution of bi-atrial activation based on sensed electrical activity using the plurality of external electrodes during delivery of atrial pacing therapy at one or more target sites, and
  - determine acceptability of the atrial pacing therapy at the or more target sites based on distribution of bi-atrial activation.

11. The system of claim 10, wherein, to determine acceptability of the atrial pacing therapy at the or more target sites based on distribution of bi-atrial activation, the computing apparatus is further configured to:
- determine an increase in amplitude of the sensed electrical activity for a predetermined number of the plurality of electrodes;
- determine a decrease in amplitude of the sensed electrical activity for a predetermined number of the plurality of electrodes;
- generate electrical heterogeneity information of the sensed electrical activity within a window extending between the determined increase in amplitude and the determined decrease in amplitude; and
- determine the distribution of bi-atrial activation based on the generated electrical heterogeneity information.

12. The system of claim 11, wherein, to generate electrical heterogeneity information of the sensed electrical activity, the computing apparatus is further configured to:
- determine a first activation delay corresponding to a posterior activation spread of the sensed electrical activity within the window;
- determine a second activation delay corresponding to an anterior activation spread of the sensed electrical activity within the window;
- determine a deviation between the first activation delay and the second activation delay; and
- determine a bi-atrial dyssynchrony score in response to the determined deviation.

13. A system for determining positioning of an atrial pacing lead for delivery of a cardiac pacing therapy, comprising:
- a plurality of external electrodes to sense electrical activity of tissue of a patient in response to atrial pacing therapy; and
- a computing apparatus comprising processing circuitry and coupled to the electrode apparatus and configured to:
  - determine a distribution of bi-atrial activation based on sensed electrical activity using the plurality of external electrodes during delivery of atrial pacing at one or more of a position adjacent the Bachman's Bundle, using a single lead within the right atrium, using a single lead within the left atrium, positioning a single lead within the atrial septum, and positioning both a single lead within the right atrium and a single lead within the left atrium, and
  - determine a target site for delivering atrial pacing therapy if a desired change in bi-atrial dyssynchrony occurs based on the distribution of bi-atrial activation.

14. The system of claim 13, wherein, to determine a target site for delivering the atrial pacing therapy if a desired change in bi-atrial dyssynchrony occurs based on the distribution of bi-atrial activation, the computing apparatus is further configured to compare the determined distribution of bi-atrial activation to a distribution of bi-atrial activation for an intrinsic rhythm.

15. The system of claim 13, wherein, to determine a distribution of bi-atrial activation based on sensed electrical activity, the computing apparatus is further configured to:
- determine an increase in amplitude of the sensed electrical activity for a predetermined number of the plurality of electrodes;

determine a decrease in amplitude of the sensed electrical activity for a predetermined number of the plurality of electrodes;

generate electrical heterogeneity information of the sensed electrical activity within a window extending between the determined increase in amplitude and the determined decrease in amplitude; and determine the distribution of bi-atrial activation based on the electrical heterogeneity information.

16. The system of claim 15, wherein, to generate electrical heterogeneity information of the sensed electrical activity, the computing apparatus is further configured to:

determine a first set of activation times corresponding to a posterior set of electrodes from the sensed electrical activity within the window;

determine a second set of activation times corresponding to an anterior set of electrodes from the sensed electrical activity within the window;

determine a standard deviation of activation times for a combination of the first set of activation times and the second set of activation times; and determine a bi-atrial dyssynchrony score based on the determined standard deviation.

17. The system of claim 16, wherein, to determine a target site for delivering the atrial pacing therapy if a desired change in bi-atrial dyssynchrony occurs based on the distribution of bi-atrial activation, the computing apparatus is further configured to determine whether the bi-atrial dyssynchrony score corresponds to a predetermined reduction in an intrinsic rhythm bi-atrial dyssynchrony score.

18. The system of claim 16, wherein, to determine a target site for delivering the atrial pacing therapy if a desired change in bi-atrial dyssynchrony occurs based on the distribution of bi-atrial activation, the computing apparatus is further configured to:

compare the determined bi-atrial dyssynchrony score to an intrinsic rhythm bi-atrial dyssynchrony score;

determine a change in bi-atrial dyssynchrony in response to the comparing; and determine that there is the desired change in bi-atrial dyssynchrony in response to the determined change in bi-atrial dyssynchrony for two or more of positioning a single lead at a position adjacent the Bachman's Bundle, positioning a single lead within the right atrium, positioning a single lead within the left atrium, positioning a single lead within the atrial septum, and positioning both a single lead within the right atrium and a single lead within the left atrium.

19. A system for use in evaluation of atrial pacing therapy, comprising:

a plurality of external electrodes to sense electrical activity of tissue of a patient from; and a computing apparatus comprising processing circuitry and coupled to the electrode apparatus and configured to:

monitor electrical activity using the plurality of external electrodes, and generate bi-atrial electrical heterogeneity information based on the monitored electrical activity.

20. The system of claim 19, wherein, to generate bi-atrial electrical heterogeneity information based on the monitored electrical activity, the computing apparatus is further configured to determine a plurality of atrial activation times based on the monitored electrical activity.

21. The system of claim 19, wherein, to generate bi-atrial electrical heterogeneity information based on the monitored electrical activity, the computing apparatus is further configured to:

determine an increase in amplitude of the sensed electrical activity for a predetermined number of the plurality of electrodes;

determine a decrease in amplitude of the sensed electrical activity for a predetermined number of the plurality of electrodes;

generate electrical atrial activation information from the sensed electrical activity within a window extending between the determined increase in amplitude and the determined decrease in amplitude; and determine the bi-atrial electrical heterogeneity information based on the electrical atrial activation information.

22. The system of claim 19, wherein, to generate bi-atrial electrical heterogeneity information based on the monitored electrical activity, the computing apparatus is further configured to:

determine a first set of atrial activation times corresponding to a posterior set of electrodes based on the monitored electrical activity;

determine a second set of atrial activation times corresponding to an anterior set of electrodes based on the monitored electrical activity; and determine a standard deviation of activation times for a combination of the first set of activation times and the second set of activation times.

23. The system of claim 19, wherein, to generate bi-atrial electrical heterogeneity information based on the monitored electrical activity, the computing apparatus is further configured to generate bi-atrial electrical heterogeneity information based on the monitored electrical activity during delivering of pacing therapy at a plurality of atrial pacing sites, wherein the computing apparatus is further configured to determine a target atrial pacing site from the plurality of atrial pacing sites based on the bi-atrial electrical heterogeneity information.

24. The system of claim 19, wherein, to generate bi-atrial electrical heterogeneity information based on the monitored electrical activity, the computing apparatus is further configured to:

generate paced bi-atrial electrical heterogeneity information based on the monitored electrical activity during delivering of pacing therapy; and generate intrinsic bi-atrial electrical heterogeneity information based on the monitored electrical activity without delivery of pacing therapy during intrinsic cardiac activation, and wherein the computing apparatus is further configured to compare the paced bi-atrial electrical heterogeneity information to the intrinsic bi-atrial electrical heterogeneity information.

* * * * *